(12) United States Patent
Kato et al.

(10) Patent No.: US 6,264,989 B1
(45) Date of Patent: Jul. 24, 2001

(54) SPHERICAL SINGLE-SUBSTANCE PARTICLES, MEDICINES AND FOODSTUFFS CONTAINING THE PARTICLES, AND METHOD OF PRODUCTION THEREOF

(75) Inventors: Hisayoshi Kato; Nagayoshi Myo; Ikuo Tanai, all of Tokyo; Yusuke Suzuki, Osaka; Toshiro Fujii; Yoshitaka Tomoda, both of Hyogo, all of (JP)

(73) Assignees: Freund Industrial Co., Ltd., Tokyo; Shionogi & Co., Ltd., Osaka, both of (JP)

( * ) Notice: Subject to any disclaimer, the term of this patent is extended or adjusted under 35 U.S.C. 154(b) by 0 days.

(21) Appl. No.: 09/463,327

(22) PCT Filed: Jul. 23, 1998

(86) PCT No.: PCT/JP98/03298

§ 371 Date: Jan. 24, 2000

§ 102(e) Date: Jan. 24, 2000

(87) PCT Pub. No.: WO99/04760

PCT Pub. Date: Feb. 4, 1999

(30) Foreign Application Priority Data

Jul. 23, 1997 (JP) .................................................... 9-211184
Feb. 19, 1998 (JP) .................................................... 10-52655

(51) Int. Cl.$^7$ ................................. A61K 9/16; A61K 9/50

(52) U.S. Cl. ........................... 424/490; 424/489; 424/493; 424/439; 424/451; 424/496; 424/497; 427/2.18; 427/2.15; 427/212; 427/213; 427/214; 427/242

(58) Field of Search .................................... 424/489, 496, 424/490, 497, 493, 439; 727/2.18, 2.15, 212, 213, 214, 242; 514/951

(56) References Cited

U.S. PATENT DOCUMENTS

| | | | |
|---|---|---|---|
| 3,928,566 | * 12/1975 | Briggs et al. | 424/94 |
| 4,632,843 | * 12/1986 | Pich et al. | 427/3 |
| 5,290,569 | * 3/1994 | Nagafuzi et al. | 424/490 |
| 5,618,562 | * 4/1997 | Saito et al. | 424/489 |
| 5,792,507 | * 8/1998 | Kato et al. | 427/2.18 |

FOREIGN PATENT DOCUMENTS

| | | |
|---|---|---|
| 5-229961 | 9/1993 | (JP) . |
| 6-192074 | 7/1994 | (JP) . |
| 6-205959 | 7/1994 | (JP) . |
| 7-173050 | 7/1995 | (JP) . |
| 9-175999 | 7/1997 | (JP) . |
| 9-263589 | 10/1997 | (JP) . |

* cited by examiner

*Primary Examiner*—James M. Spear
*Assistant Examiner*—Liliana Di Nola Baron
(74) *Attorney, Agent, or Firm*—Foley & Lardner

(57) ABSTRACT

The present invention relates to a process for producing a spherical particle comprising an aggregate of particles containing at least 95% of a water-soluble single substance having a viscosity of 10 mPa.s or less as determined in the form of a saturated aqueous solution, the process comprising: preparing moist spherical particles of the single substance by charging, as cores, crystalline particles or granulated particles of the single substance on a rotary disc in a processing vessel of a centrifugal tumbling granulating apparatus, wherein the granulated particles are prepared by granulating a powder of the single substance, and dispersing over the cores a powder of the single substance and simultaneously spraying on the cores a liquid such as water or the like while supplying slit air to provide a fluidized condition; and then fixation treating the moist spherical particles by drying them while spraying an aqueous solution of the single substance or the like on the spherical particles in a fluidized bed apparatus; to the spherical particle produced by the process; and to a pharmaceutical preparation and a food containing the spherical particle.

20 Claims, 5 Drawing Sheets and a method for producing the spherical
SPHERICAL SINGLE-SUBSTANCE PARTICLES, MEDICINES AND FOODSTUFFS CONTAINING THE PARTICLES, AND METHOD OF PRODUCTION THEREOF This application is a 371 of PCT/JP98/03298 filed Jul. 23, 1998.

FIELD OF THE INVENTION

The present invention relates to spherical single-substance particles having good surface smoothness and low abrasiveness and a method for producing the same. More specifically, the present invention relates to spherical particles comprising a sugar alcohol, sodium chloride, vitamin C or the like, which is useful for coating granulation in the preparation of medicines and foodstuffs and to a method of the production thereof.

RELATED BACKGROUND ART

Spherical particles used as raw materials of pharmaceuticals have been mainly used as seeds of sustained-release preparations and enteric coated preparations. Examples of such spherical particles for pharmaceutical use include "Sugar Spheres" made mainly of sucrose/corn starch, which is prescribed in the "National Formulary (NF)"; and purified sucrose spheres (e.g., "Nonpareil-103", a tradename of Freund Industrial Co., Ltd.), sucrose/starch spheres (e.g., "Nonpareil-101", a tradename of Freund Industrial Co., Ltd.) and microcrystalline cellulose spheres (e.g., "Celphere" made by Asahi Chemical Industry Co., Ltd.), which are prescribed in the Japanese Pharmaceutical Excipients (JPE 1998).

All of the substances serving as the raw materials of such spherical particles have physiochemical properties suited for the formation of spherical shapes. For example, a series of commercial products sold under the aforementioned tradename "Nonpareil®", which have cores made of granulated sugar having an octahedral to dodecahedral monoclinic crystalline structure, are suitable for the sphere formation, because they can also effectively act as binders in the form of aqueous solutions. Commercial product sold under the aforementioned tradename "Celphere®", which is a spherical particle without a core, can also be formed into spheres readily, because the raw component crystalline cellulose thereof has a short fibrous form.

The commercial product "Nonpareil-103®", for example, is known to be produced by charging granulated sugar as a core into a centrifugal tumbling apparatus (e.g., "CF-Granulator" manufactured by Freund Industrial Co., Ltd.; hereinafter, simply referred to as "CF apparatus"), dispersing sucrose microparticles or powders over the granulated sugar core while spraying an aqueous sucrose solution as a binder on the core to thereby coat the granulated sugar with sucrose, and then granulating the resultant coated granulated sugar into spheres. Thus, the product "Nonpareil-103®" can be said to consist of 100% sucrose, since granulated sugar has the same chemical composition as that of sucrose.

The commercial product "Nonpareil-101®" is known to be produced by charging granulated sugar as a core into CF apparatus, dispersing microparticles or powders of a sucrose/starch mixture over the granulated sugar core while spraying an aqueous solution of a sucrose/starch mixture as a binder on the core to thereby coat the granulated sugar with the sucrose/starch mixture, and then granulating the resultant coated granulated sugar into spheres. In the product "Nonpareil-103®", the content ratio of sucrose to starch is 65–85%:35–15%.

Another type of spherical particle granulated from a core and the method for the production thereof is disclosed in Japanese Patent Application Laid-open No. 5-229961, in which the spherical particle comprises a mixture of a water-soluble substance (e.g., lactose) and a water-insoluble substance (e.g., cellulose) and has a particle diameter of 0.1–1 mm.

These spherical particles can be used for pharmaceutical preparation. However, many medicinal agents often react with the raw substances of the spherical particles to cause a brown discoloration such as Maillard reaction. Therefore, upon use with such medicinal agents, complicated tests are required for confirming the compatibility of the raw substances of the spherical particles with the medicinal agents.

Lactose has been focused on as a raw material of a spherical particle for pharmaceutical preparation, because it is less reactive with various medicinal agents and therefore has a low tendency to cause Maillard reaction with the medicinal agents. For example, Japanese Patent Application Laid-open No. 6-205959 discloses a lactose spherical particle and a method for producing it, in which the finished spherical particle comprising at least 95% lactose and has a longer diameter/shorter diameter ratio of 1.2 or lower, and as an aggregate, exerts a bulk density of 0.7 g/mL or larger and an angle of repose of 35 degree or less.

DISCLOSURE OF THE INVENTION

In the case of lactose which is less reactive with medicinal agents, however, one has not succeeded as yet in producing spherical particles of lactose alone with high sphericity and low abrasiveness in the industrial scale, because lactose itself has no function as a binder.

For example, in the method disclosed in Japanese Patent Application Laid-open No. 5-229961, when lactose is combined with crystalline cellulose at a mixing ratio of at least 95% lactose, particles can be obtained which macroscopically appear spherical. However, when the surface of the individual spherical particles is observed under a scanning electron microscope, lactose powder particles are clung to the surface unevenly. Therefore, when such spherical particles are further coated with a medicinal agent to produce a sustained-release preparation, such unevenness undesirably leads to greater abrasiveness, resulting in unavoidable reduction in yields (i.e., coating efficiency and granulating efficiency).

Likewise, with respect to the method disclosed in Japanese Patent Application Laid-open No. 6-205959, the present inventors have also found such a disadvantage that the lactose content of 95% or greater causes the phenomenon of microscopic surface roughness of the finished spherical particles.

The disadvantages as mentioned above are also true for substances other than lactose, as illustrated in the drawings attached. For example, in the case of a sugar alcohol, sodium chloride and vitamin C, it was impossible to prepare smooth-surfaced spherical particles consisting essentially of the single substance.

Accordingly, an object of the present invention is to provide a novel spherical particle consisting essentially of a single substance and a method for producing the spherical particles, which can overcome the drawbacks associated with the prior art spherical particles comprising sucrose (or a sucrose/starch mixture), crystalline cellulose, a lactose/crystalline cellulose mixture or the like. Another object of the present invention is to provide a food and a pharmaceutical preparation comprising the spherical particles.

The present inventors have further studied on improving the surface smoothness and reducing the abrasiveness of spherical particles consisting essentially of a single substance. As a result, the inventors have succeeded in the establishment of a method in which moist spherical single-substance particles granulated in the aforementioned CF apparatus are sprayed with an aqueous solution of the single substance in a fluidized bed and dried to conduct the fixation treatment of the surface of the spherical particles. This success led to the accomplishment of the present invention.

The present invention encompasses the following aspects and embodiments.

(1) A spherical particle comprising a granulated particle containing at least 95 wt % of a water-soluble single substance which has a viscosity of 10 mPa.s or less as determined in the form of a saturated aqueous solution, the spherical particle having an aspect ratio of 1.2 or less and, as an aggregate, having a bulk density of 0.65 g/mL or more and an angle of repose of 35 degree or less.

(2) A spherical particle comprising a granulated crystalline particle containing at least 95 wt % of a water-soluble single substance which has a viscosity of 10 mPa.s or less as determined in the form of a saturated aqueous solution, the spherical particle having an aspect ratio of 1.2 or less and, as an aggregate, having a bulk density of 0.65 g/mL or more, an angle of repose of 35 degree or less and an abrasiveness of 1.0% or less.

(3) The spherical particle of item (1) or (2), wherein the single substance is one selected from the group consisting of a sugar alcohol, vitamin C and sodium chloride.

(4) The spherical particle of item (3), wherein the sugar alcohol is D-mannitol and/or erythritol.

(5) The spherical particle of item (3), wherein the vitamin C is L-ascorbic acid and/or sodium L-ascorbate.

(6) The spherical particle of item (1), wherein the single substance comprises at least 95 wt % of xylitol.

(7) A process for producing the spherical particles of any one of items (1) to (6), the process comprising the steps of:
preparing moist spherical particles of a water-soluble single substance having a viscosity of 10 mPa.s or less as determined in the form of a saturated aqueous solution, by charging, as cores, granulated particles of the single substance on a rotary disc in a processing vessel of a centrifugal tumbling apparatus, wherein the granulated particles are prepared by granulating a powder of the single substance; and then dispersing a powder of the single substance over the cores and simultaneously spraying on the cores at least one liquid selected from the group consisting of water, an aqueous solution of the single substance and a diluted aqueous solution of a water-soluble polymer, while both rotating the rotary disc and supplying slit air into the vessel; and
fixation-treating the moist spherical particles by drying them while spraying an aqueous solution of the single substance and/or a diluted aqueous solution of the water-soluble polymer a fluidized bed apparatus.

(8) A process for producing the spherical particles of any one of items (1) to (6), the process comprising the steps of:
preparing moist spherical particles of a water-soluble single substance having a viscosity of 10 mPa.s or less as determined in the form of a saturated aqueous solution, by charging, as cores, crystalline particles of the single substance on a rotary disc in a processing vessel of a centrifugal tumbling apparatus; and then dispersing powdery particles of the single substance over the cores and simultaneously spraying on the cores at least one liquid selected from the group consisting of water, an aqueous solution of the single substance and a diluted aqueous solution of a water-soluble polymer, while both rotating the rotary disc and supplying slit air into the vessel; and
fixation-treating the moist spherical particles by drying them while spraying an aqueous solution of the single substance and/or a diluted aqueous solution of the water-soluble polymer in a fluidized bed apparatus.

(9) A process for producing spherical particles each consisting essentially of an aggregate of sodium chloride crystal microparticles containing at least 95 wt % of sodium chloride, the process comprising the steps of:
preparing moist spherical particles of sodium chloride by charging, as cores, sodium chloride crystal particles on a rotary disc in a processing vessel of a centrifugal tumbling apparatus; and then dispersing sodium chloride crystal microparticles which were previously been crushed over the cores and simultaneously spraying on the cores at least one liquid selected from the group consisting of water, an aqueous sodium chloride solution and a diluted aqueous solution of a water-soluble polymer, while both rotating the rotary disc and supplying slit air into the vessel; and
drying the moist spherical particles in a fluidized bed apparatus.

(10) A process for producing spherical particles consisting essentially of xylitol crystal particles, the process comprising the steps of:
preparing moist spherical particles of xylitol by charging, as cores, xylitol crystal particles on a rotary disc in a processing vessel of a centrifugal tumbling apparatus; and then dispersing powdery xylitol particles over the cores and simultaneously spraying on cores at least one liquid selected from the group consisting of water, an aqueous xylitol solution and a diluted aqueous solution of a water-soluble polymer, while both rotating the rotary disc and supplying slit air into the vessel; and
fixation-treating the moist spherical particles by drying them while spraying either a shellac-containing aqueous ethanol solution or vinyl acetate resin-containing ethyl acetate in a fluidized bed apparatus.

(11) The process of item (7) or (8), wherein the single substance is D-mannitol and/or erythritol.

(12) The process of item (7) or (8), wherein the single substance is L-ascorbic acid and/or sodium L-ascorbate.

(13) A spherical particle for use in the production of a food preparation, comprising the spherical particle of any one of items (1) to (6).

(14) A spherical particle for coating granulation in the production of a food, comprising the spherical particle of any one of items (1) to (6).

(15) A spherical particle for coating granulation in the production of a pharmaceutical preparation, comprising the spherical particle of any one of items (1) to (6).

(16) The spherical particle for coating granulation in the production of a pharmaceutical preparation of item (15), wherein the spherical particle is a substance comprising D-mannitol.

(17) A pharmaceutical preparation comprising the spherical particle of item (15) or (16).

(18) The pharmaceutical preparation of item (17), which contains phenylpropanolamine hydrochloride as a pharmaceutically active component.

(19) The pharmaceutical preparation of item (17) or (18), wherein the pharmaceutical preparation is in the form of granules or capsules.

(20) A process for producing a pharmaceutical preparation, comprising using the spherical particles for coating granulation of item (15) or (16) as a carrier.

The single substance used in the present invention, when used for the production of a pharmaceutical preparation, is preferably one compliant with the standard for a single substance of the Japanese Pharmacopoeia (hereinafter, simply referred to as "JP") (e.g., the 13th Amendment of JP), but it is not limited thereto.

As used herein, the term "single substance" refers to any pure, single chemical substance, as well as a mixture of substances known to be of the same type each other, such as a mixture of L-ascorbic acid and sodium L-ascorbate, both which are known as vitamin C and have chemically and physiologically same properties, and a mixture of D-mannitol and erythritol, both which are known as sugar alcohols and have chemically and physiologically same properties.

The term "single substance" may also refer to a single substance as defined above which contains other substance in an amount not exceed 5 wt %.

The properties required to the single substance used in the present invention include a crushable property into powder and solubility in water (because it is also used in the form of an aqueous solution). When a crystalline single substance is used, the crystals of the single substance grow around a core into a sphere with layering onto the surface of the core, whereby most of spherical particles have a crystalline structure.

Moreover, the single substance is also required to have a viscosity of 10 mPa.s or less as determined in the form of a saturated aqueous solution. In particular, a saturated aqueous solution of the single substance is necessary to have a viscosity of 10 mPa.s or less as measured with a B-type viscometer at 25–45° C.

The viscosities of saturated aqueous solutions of different single substances measured with a B-type viscometer are shown in Table 1.

TABLE 1

| Single substance | Viscosity (mPa · s) |
| --- | --- |
| Mannitol | |
| 20 wt % aqueous solution, at 25° C. | 5.5 |
| 30 wt % aqueous solution, at 45° C. | 4.8 |
| L-ascorbic acid | |
| 24 wt % aqueous solution, at 25° C. | 5.2 |
| 40 wt % aqueous solution, at 45° C. | 5.5 |
| Sodium chloride | |
| 26 wt % aqueous solution, at 25° C. | 5.3 |
| 27 wt % aqueous solution, at 45° C. | 5.0 |
| Lactose | |
| 20 wt % aqueous solution, at 25° C. | 6.3 |
| 30 wt % aqueous solution, at 45° C. | 5.1 |
| Granulated sugar (i.e., Sucrose) | |
| 67 wt % aqueous solution, at 25° C. | 156 |
| 71 wt % aqueous solution, at 45° C. | 150 |

When compared between the single substances of Table 1, it is found that aqueous solutions of granulated sugar have remarkably large viscosities.

Heretofore, there are some instances where granulated sugar is used as a binder, in which the viscosities of the aqueous solutions of granulated sugar used as binders are generally about 100 mPa.s and, even when warmed, about 40 mPa.s. In contrast, the viscosity required to the aqueous solution of the single substance of the present invention is lower than those for the prior art binders and therefore is not encompassed within the scope of the prior art binders.

Examples of the single substance include a sugar alcohol, vitamin C, sodium chloride and lactose. Among them, a sugar alcohol and sodium chloride are preferable as the raw materials of spherical particles for coating granulation of pharmaceuticals because of having no aldehyde groups that may cause Maillard reaction. These substances are also preferable as the raw materials of spherical particles for use in food preparation.

Examples of the sugar alcohol used as the single substance include D-mannitol, erythritol and a mixture thereof, and especially preferably D-mannitol. Examples of the vitamin C used as the single substance include L-ascorbic acid, sodium L-ascorbate and a mixture of the both.

The granulated or crystalline particle of a single substance (hereinafter, also referred to as "granulated or crystalline single-substance particle" or "single-substance granule or crystalline particle") used as the core in the present invention has a particle size passing through a 500 μm sieve, particularly preferably from that passing through a 300 μm sieve to that held on a 150 μm sieve. The granulated or crystalline single-substance particle with a larger particle size will yield a finished spherical particle with a larger particle size.

The powdery particle of a single substance (hereinafter, also referred to as "powdery single-substance particle" or "single-substance powder") used for the preparation of the spherical particle in the present invention is a powdery particle of a single substance crystal having a particle size passing through a 75 μm sieve, and preferably that having a particle size not larger than 1/5 to 1/10 the average particle size of the granulated or crystalline single-substance particle core. The powdery single-substance particle with a smaller particle size is preferred, and a powdery microparticle of a single-substance crystal can be used, such as fine powder of a sugar alcohol, vitamin C or sodium chloride. When the granulated or crystalline single-substance particles are compressed or absorb moisture to be solidified, they are subjected to grinding into fine powder of a particle size of 75 μm or less using a known grinding apparatus before use.

The granulated single-substance particle of the present invention can be prepared by granulating a powder of the single substance. In this process, the single-substance powder is granulated while supplying water or an aqueous solution of the single substance. Therefore, the single substance has to be water-soluble.

The granulated particle used as a core in the method of the present invention may be prepared by, for example, an extruding granulation method, which comprises charging a powder of a single substance into a kneader, supplying water or an aqueous solution of the single substance thereto to knead the resultant product, extruding-granulating the resultant product, drying the resultant granules and then sieving the granules, thereby giving the desired granulated particles.

When a wet-type agitation-granulation method is employed, the granulated particles can be produced by charging a powder of a single substance into an agitation granulating apparatus ("High-Speed Mixer" manufactured by Fukae Powtec Corp.), supplying water or an aqueous solution of the single substance thereto, and then subjecting the resultant mixture to agitation-granulation, thereby giving the desired granulated particles.

When a centrifugal fluidized granulation method is employed, the granulated particles can be produced by charging a powder of a single substance into a centrifugal fluidized bed granulating apparatus ("SPIR-A-FLOW®" manufactured by Freund Industrial, Co., Ltd.), supplying water or an aqueous solution of the single substance thereto, and then subjecting the resultant product to centrifugal fluidized granulation, thereby giving the desired granulated particles.

When a centrifugal tumbling granulation method is employed, the granulated particles can be produced by charging a powder of a single substance into a kneader, supplying water or an aqueous solution of the single substance thereto to knead the resultant product, granulating the resultant product with Power Mill (a tradename; manufactured by Dalton Corp.), charging the granules into a centrifugal tumbling granulating apparatus (e.g., "CF-Granulator" manufactured by Freund Industrial, Co., Ltd.), supplying water or an aqueous solution of the single substance thereto, and then subjecting the resultant product to centrifugal tumbling granulation, thereby giving the desired granulated particles.

As used herein, the term "aspect ratio" with respect to the spherical particle of a single substance of the present invention refers to a ratio of the major axis to the minor axis of the spherical particle, which is a measure of the sphericity. This major axis/minor axis ratio is determined by placing spherical particles randomly over a glass slide, photographing them, measuring both the length of the major axis (i.e., longer diameter) and the length of the minor axis (i.e., shorter diameter) taken vertical to the major axis at the midpoint for 50 particles, calculating the ratio of the longer diameter to the shorter diameter for each particle, and then averaging the determined values for the 50 particles.

The bulk density of the spherical particle of a single substance of the present invention is determined by lightly filling a 100 mL graduated cylinder (weight: W) with the spherical particles to overflowing, measuring the total weight (Wb) of the graduated cylinder with leveled spherical particles off, and then determining a value according to the formula: (Wb−W)/100. The bulk density is determined as an average of five measurements.

The angle to repose of the spherical particle of a single substance of the present invention is determined by the so-called Nogami-Sugihara method as described in Japanese Patent Application Laid-open No. 6-205959, and expressed as an average of five measurements. The measuring apparatus used for the determination of angle of repose is shown in FIG. 2, which is composed of four glass plates each jointed as shown in the drawing. The determination of angle of repose with this apparatus is performed by gently pouring about 200 ml of sample particles along the side (A) onto the side (B) (a glass bottom) using a funnel, continuing to pour until the sample particles begin to flow out from the front opening of the side (B), and then measuring using a protractor an angle between the side (B) (i.e., horizontal surface) and the tilting upper surface of the sample particle layer on the side (B) at the time when the sample particles begin to flow out.

The abrasiveness of the spherical particle of a single substance of the present invention in an aggregated form is a numerical value for the degree of friability of the particle surface which occurs upon the impact between the particles or between the particles and the vessel wall without disruption of the particles. It can be determined by placing a given amount of the spherical particles into a vessel, applying a rotational or vibrating movement to the vessel for a period of time, recovering the particles from the vessel, separating abraded powdery matters from the particles by sieving, and calculating a weight percentage of the remaining particles to the initially present particles.

Specifically, the abrasiveness can be determined as follows: a given amount of the spherical particles (Wt; e.g., about 10 g) is weighed precisely, the particles are placed into a stainless steel vessel of 32 mm (inner diameter)×65 mm (depth), the vessel is shaken at 1,100 rpm for just 10 minutes using a mixer mill (e.g., a product by SPEX), the resultant particles are sieved with a 300 μm sieve, and the weight of the remaining particles (Ws g) was measured precisely. The abrasiveness (%) is determined according to the following formula:

$$(Wt-Ws)/Wt \times 100 = \%.$$

The abrasiveness is preferably 1.0% or lower, and more preferably 0.5% or lower.

The fixation treatment employed in the process for producing the spherical single-substance particles of the present invention is a treatment both for making the surface of the individual particles smooth and for improving the abrasiveness of the particles.

The water-soluble polymer used for the production of the spherical single-substance particles of the present invention includes, but not limited to, animal-derived polymers (e.g., gelatin and casein), vegetable-derived polymers (e.g., alginic acid, carrageenan and hemicellulose), celluloses (e.g., carboxymethyl cellulose, methyl cellulose, hydroxyethyl cellulose, hydroxypropyl cellulose and hydroxypropylmethyl cellulose), synthetic polymers (e.g., polyvinyl pyrrolidone, polyacrylates, polyvinyl alchol), and pullulan.

The water-soluble polymer is used in the form of a diluted aqueous solution. The concentration of the diluted aqueous solution may be decided experimentally for each water-soluble polymer so that the aqueous solution of the water-soluble polymer exerts a weakened binding strength as a binder.

In the present invention, the spherical single-substance particles may carry a medicinal agent (i.e., an agent having a pharmaceutically active effect) in an amount less than 5%. The medicinal agent may be suitably selected from the various types of medicinal agents including water-soluble vitamins and antipyretic analgesics. However, the spherical particle may consist of a single substance alone.

In the present invention, the spherical single-substance particles may also contain a food component or a food additive in an amount less than 5%. The food component or a food additive may be suitably selected from those of various types, including water-soluble vitamins and flavoring agents. However, the spherical particle may consist of a single substance alone.

The centrifugal tumbling apparatus applicable for the production of the spherical single-substance particles of the present invention is one equipped with the following members: a smooth-surfaced rotary disc mounted on the bottom of the processing vessel, which is rotatable substantially in the horizontal direction; a rotating shaft for causing to rotate the rotary disc; a slit that is a doughnut-shaped space formed between the inner wall of the processing vessel and the circumference of the rotary disc; a slit air supplying device for supplying slit air from the slit into the processing vessel; a spray nozzle for spraying at least one liquid selected from water, an aqueous solution of a single substance and an a diluted aqueous solution of a water-soluble polymer, on a substance to be treated (i.e., a crystalline or granulated single-substance particle) in the processing vessel; and a powder dispersing device for dispersing a powdery material onto the substance to be treated. An example of this apparatus is "CF-Granulator" manufactured by Freund Industrial, Co., Ltd. (hereinafter, simply referred to as "CF apparatus") as illustrated in FIG. 1 (slit air supplying device being not shown).

CF apparatus belongs to the category called "coating granulation apparatus". However, the coating granulation apparatus applicable in the present invention is not limited to CF apparatus, and any other type of apparatus may be used provided that it has the fundamental construction as mentioned above. CF apparatus may be modified in various fashions. For example, the rotating shaft may be mounted on the rotary disc; the rotary disc may have an edge curved upward or of a flat type; or the rotary disc may have an upper surface of which the center portion has protrusions provided that at least the portion of the upper surface in contact with the powder is smooth.

The fluidized bed apparatus applicable for the production process of the present invention is one equipped with the following components: a storage vessel for containing the moist spherical particles produced in the centrifugal tumbling apparatus; a fluidizing air supplying device for supplying fluidizing air so as to fluidize the spherical particles; and a spray nozzle for spraying on the spherical particles an aqueous solution of the single substance and/or a diluted aqueous solution of a water-soluble polymer. As such a fluidized bed apparatus, "Flow Coater®" manufactured by Freund Industrial, Co., Ltd. (hereinafter, simply referred to as "FL apparatus") is available. FL apparatus belongs to the category called "fluidized bed coating granulation apparatus". The fluidized bed apparatus available in the present invention is not limited to FL apparatus, and any other type of apparatus may also be used, such as fluidized bed apparatus equipped with a rotary disc with an air vent, such as FL apparatus equipped with a rotor container and a centrifugal fluidized bed coating granulation apparatus, "SPIR-A-FLOW®" manufactured by Freund Industrial, Co., Ltd.

In the centrifugal tumbling apparatus used for the production of the spherical single-substance particles of the present invention, the liquid to be sprayed may be water optionally containing a small amount of a water-soluble polymer dissolved therein, an aqueous solution of the single substance. These liquids may contain a small amount of an additive such as a coloring agent. However, water alone is generally preferred.

The production process of the spherical single-substance particles of the present invention is described in detail below with reference to the drawing of CF apparatus shown in FIG. 1.

In FIG. 1, the individual numerals refer to the following components: 1 granulating vessel; 2 rotary disc; 2a edge of the rotary disc; 3 rotating shaft; 4 slit; 4a slit air; 5 air chamber; 6 dehumidifier; 7 heat exchanger; 8 powdery single-substance particle; 9 dispersing device; 10 spraying liquid; 11 tank; 12 constant flow pump; 13 spray nozzle; 14 spraying air; 15 product ejection device; 16 stator cover; 17 air served as the slit air.

In CF apparatus of FIG. 1, a rotating shaft 3 is rotated by a driving mechanism such as a motor (not shown), and air 17 is fed into a granulating vessel 1 in the form of slit air 4a through a dehumidifier 6, a heat exchanger 7 and an air chamber 5 while rotating a rotary disc 2, and at this time granulated single-substance particles (or single-substance particles) are charged on the rotary disc 2.

Simultaneously, powdery single-substance particles 8 are dispersed from a dispersing device 9 over the section near the edge 2a into which the slit air 4a is blown, and then mixed with the granulated single-substance particles (or single-substance particles) while spraying a spraying liquid 10 from a tank 11 through a spray nozzle 13 on the powdery single-substance particles (or single-substance particles) near the slit 4. In this manner, the granulation is accomplished to yield moist spherical single-substance particles.

The moist spherical single-substance particles thus prepared are then transferred to FL apparatus (not shown), where the moist particles are subjected to fixation treatment including coating and drying under spraying of a liquid (e.g., an aqueous solution of the single substance) in the fluidized state with fluidizing air, thereby yielding the spherical single-substance particles having the properties described above.

The pharmaceutical preparation of the present invention may formulated into any dosage form provided that it contains the spherical particles, and preferably granules or capsules encapsulating the granules.

In the pharmaceutical preparation, the content of the spherical particles may vary depending on the types of the pharmaceutical preparations. For example, for granules, the content of the spherical particles is about 5–90 wt %, and preferably about 20–70 wt % based on the total weight of the granule.

In the spherical single-substance particles used in the pharmaceutical preparation, the single substance may comprise D-mannitol as a main component and other sugar alcohol(s) such as xylitol and erythritol.

In the pharmaceutical preparation, a pharmaceutically active component may be present inside the spherical particles or on the surface of the spherical particles, but preferably on the surface of the spherical particles.

Examples of the pharmaceutically active component include antipyretic analgesics, medicinal agents for rhinitis, medicinal agents for circulatory system and digestive system, antibiotics, chemotherapeutic agents, vitamins, narcotic analgesics, hormonal agents, antidepressants, antiphlogistics and antipsychotics. Specific examples of the pharmaceutically active component include phenylpropanolamine hydrochloride, aspirin, ibuprofen, indomethacin, phenytoin, acetaminophen, ethenzamide, morphine, nifedipine, phenobarbital and cephalexin.

Hereinbelow, a typical process for producing the pharmaceutical preparation of the present invention is described. At first, a powdery or liquid material containing a pharmaceutically active component is coated on the spherical particles optionally in the presence of a binder to form a base medicinal layer, thus yielding crude granules. Examples of the coating method include an agitation-granulating method, a centrifugal tumbling-granulating method, a fluidized bed granulating method and a pan coating method of conventional type or ventilating-drying type.

The crude granules are then surface-treated by an appropriate manner to yield the granules. When sustained-release granules are desired, the surface treatment is performed by, for example, coating the crude granules with a powdery material optionally containing a water-repellent substance and then film-coating the resultant coated granules with a release-sustaining polymer.

Examples of the water-repellent substance include hardened glycerol/fatty acid esters (e.g., hydrogenated castor oil), higher fatty acids (e.g., stearic acid), metal salts of higher fatty acids (e.g., magnesium stearate), higher alcohols (e.g., stearyl alcohol) and waxes (e.g., carnauba wax).

Examples of the release-sustaining polymer includes ethyl cellulose, ammonio methacrylate copolymer ("EUDRAGIT RS"), shellac, highly polymerized polyvinyl alcohol, polyvinyl pyrrolidone, polyvinyl chloride, cellulose acetate, polyurethane, tetrafluoroethane, polystyrene, polypropylene, lactose polymer, hydroxyethyl methacrylate, polyethylene terephthalate, polyethylene, polyamides, polyacrylonitryl, polycarboxylic acids and cyanoacrylate polymer.

The pharmaceutical preparation comprising the spherical particles according to the present invention exerts excellent storage stability. In particular, granules and capsules that comprises spherical particles mainly comprising D-mannitol are especially preferred, because of their low reactivity with amines such as phenylpropanolamine hydrochloride.

BEST MODE FOR CARRYING OUT THE INVENTION

Hereinbelow, the present invention is illustrated in more detail with reference to the following examples; however these examples are not to be construed to limit the scope of the invention.

Example 1

D-Mannitol powder (3 kg) was charged in a granulating vessel of an agitation granulating apparatus ("High Speed Mixer FS-25 model®" manufactured by Fukae Powtec Corp.), and then subjected to agitation granulation while both supplying a 20 wt % aqueous D-mannitol solution and rotating an agitator and a chopper. After the agitation granulation was completed, the resultant granules were removed from the apparatus. The granules were dried and then sieved to give granules having particle sizes of 355–500 μm, whereby D-mannitol granules for use as cores for preparing spherical particles were obtained.

The D-mannitol granules (1 kg) were charged in a granulating vessel of a centrifugal tumbling granulating apparatus ("CF-Granulator CF-360 model" manufactured by Freund Industrial Co., Ltd.; hereinafter, simply referred to as "CF apparatus") as cores, and the rotary disc was rotated at 180 rpm while supplying slit air into the granulating vessel. Subsequently, spray granulation was performed by spraying a 20 wt % aqueous D-mannitol solution (400 mL) under pressure at 0.8 kg/cm$^2$ while dispersing D-mannitol powder having an average particle size of 7.4 μm (1 kg) over the D-mannitol granules at a feed rate of 25 g/min, thereby yielding moist spherical D-mannitol particles.

The moist spherical D-mannitol particles were charged in a granulating vessel of a fluidized bed granulating apparatus ("Flow Coater FL-5 model®" manufactured by Freund Industrial Co., Ltd.; hereinafter, simply referred to as "FL apparatus), and then spray coated with a 20wt % aqueous D-mannitol solution (1 kg) at a rate of 40 mL/min while drying at 60° C., thereby yielding spherical D-mannitol particles having particle sizes of 500–710 μm (yield: 84.5%).

Figure 5:
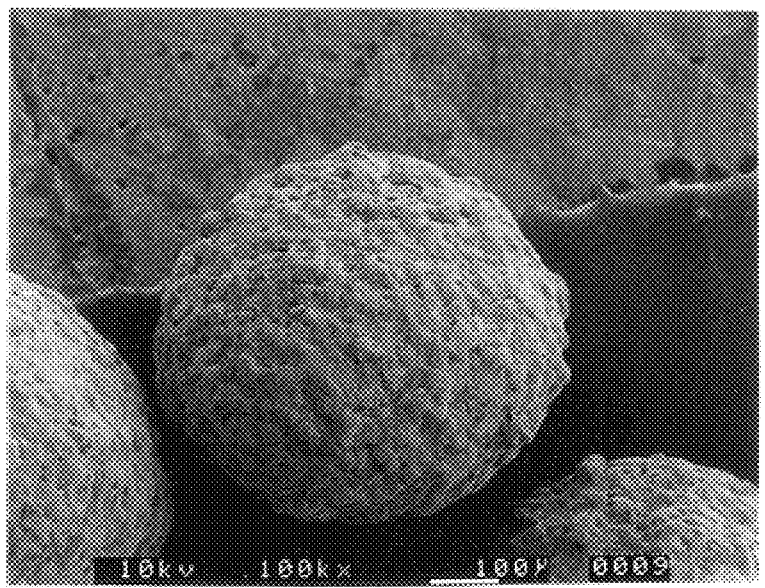
FIG. 5 is a photograph showing the surface condition of a spherical single-substance (D-mannitol) particle according to the present invention, as observed under an electron microscope.

The spherical particles had an aspect ratio of 1.09 and, as an aggregate, had a bulk density of 0.70 g/mL and an angle of repose of 31 degree. The individual spherical particles had a smooth surface as shown in FIG. 5, and had a friability of 0.27%.

Example 2

D-Mannitol powder (2 kg) was charged in a kneader and water (200 g) was added thereto. The mixture was kneaded for 15 min. and then disintegrated with a power mill equipped with a 4 mm screen to give moist powder. The moist powder was charged in CF apparatus, the rotary disc was rotated at 200 rpm, and the powder was then subjected to spray granulation while spraying water (70 mL) at a rate of 5 mL/min. The resultant granules were dried and then sieved to give granules having particle sizes of 212–355 μm, whereby D-mannitol granules for use as cores for preparing spherical particles were obtained.

The same procedures as in Example 1 was performed, except that the D-mannitol granules (212–355 μm) were used as cores in place of the D-mannitol granules (355–500 μm), thereby yielding spherical D-mannitol particles having particle sizes of 300–500 μm (yield: 80.2%).

The spherical particles had an aspect ratio of 1.10, a bulk density of 0.72 g/mL and an angle of repose of 32 degree. The individual spherical particles also had a smooth surface just as that shown in FIG. 5, and had a friability of 0.34%.

Example 3

The D-Mannitol granule cores (212–355 μm) (1 kg) obtained in Example 2 were charged in CF apparatus, and the rotary disc was rotated at 180 rpm while supplying slit air into the granulating vessel. Subsequently, spray granulation was performed for 40 min. by spraying a 1 wt % aqueous solution (240 mL) of hydroxypropyl cellulose ("HPC-L" made by Nippon Soda Co., Ltd.) under pressure at 0.8 kg/cm$^2$ while dispersing D-mannitol powder having an average particle size of 7.4 μm (1 kg) to the cores at a feed rate of 25 g/min. The resultant granules were dried and then sieved, thereby yielding moist spherical D-mannitol particles.

The moist spherical particles were charged in a granulating vessel of FL apparatus, and then spray coated with a 20wt % aqueous D-mannitol solution (1 kg) at a rate of 40 mL/min while drying at 60° C., thereby yielding spherical D-mannitol particles having particle sizes of 300–500 μm (yield: 78.5%).

The spherical particles had an aspect ratio of 1.15, a bulk density of 0.71 g/mL and an angle of repose of 33 degree. The individual spherical particles also had a smooth surface just as that shown in FIG. 5, and had a friabiluty of 0.35%.

Example 4

Crystalline vitamin C (L-ascorbic acid) (500 g), which was previously been sieved to 180–355 μm, was charged as cores on the rotary disc in CF apparatus and the rotary disc was rotated at 200 rpm, while supplying slit air into the granulating vessel. Subsequently, spray granulation was performed by spraying water on the cores at a rate of 10 mL/min. under pressure at 0.8 kg/cm$^2$ while dispersing powdery vitamin C (L-ascorbic acid) (1550 g) with an average particle size of 21.4 μm over the cores at a feed rate of 60 g/min., thereby giving moist spherical particles.

Figure 7:
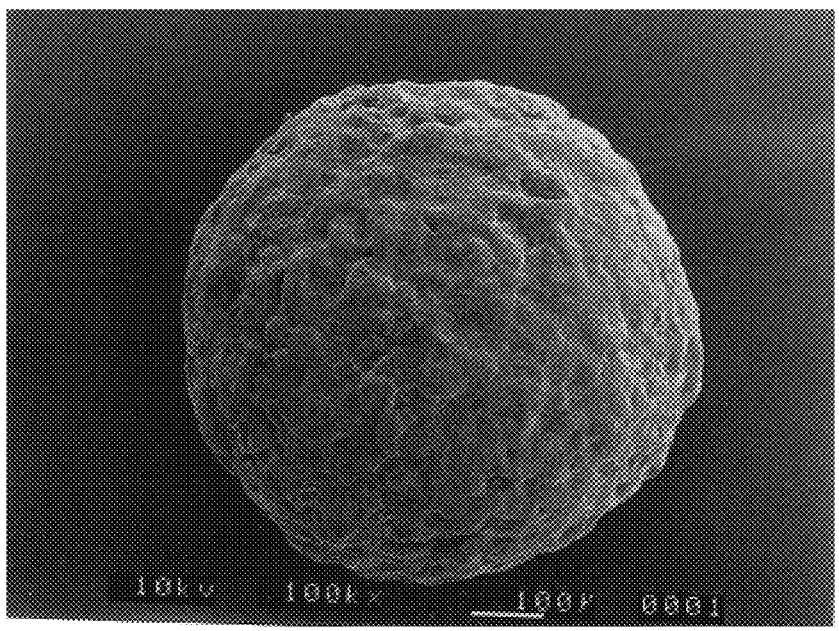
FIG. 7 is a photograph showing the surface condition of a spherical single-substance (L-ascorbic acid) particle according to the present invention, as observed under an electron microscope.

The moist spherical particles were charged in FL apparatus, and then dried under fluidized conditions at 60° C. After the drying was completed, vitamin C (L-ascorbic acid) was coated on the dried spherical particles under the same fluidized conditions by spraying a 20wt % aqueous vitamin C solution (800 g) at a rate of 40 mL/min and then drying the resultant particles, thereby yielding spherical particles consisting essentially of vitamin C (L-ascorbic acid) alone having particle sizes of 355–600 μm (yield: 75%). The spherical particles had an aspect ratio of 1.10 and, as an aggregate, had a bulk density of 0.86 g/mL and an angle of repose of 31 degree. The individual spherical particles had a smooth surface as shown in FIG. 7, and had a friability of 0.46%.

Example 5

Powdery vitamin C (crystalline sodium L-ascorbate) (1 kg), which was previously been passed through a 75 μm sieve, was mixed with a 10 wt % aqueous HPC-L solution (100 mL). The mixture was kneaded in a kneader, extruded through a 0.5 mm screen to give granules. The granules were dried, further granulated and then sieved to give vitamin C (sodium L-ascorbate) granules having particle sizes of 500–710 μm.

The vitamin C (sodium L-ascorbate) granules (500 g) were charged as cores on the rotary disc in CF apparatus and the rotary disc was rotated at 200 rpm while supplying slit air into the granulating vessel. Subsequently, spray granulation was performed by spraying water on the cores at a rate of 10 mL/min. under pressure at 0.8 kg/cm$^2$ while dispersing powdery vitamin C (crystalline sodium L-ascorbate) (1000 g) with an average particle size of 21.4 μm over the cores at a feed rate of 60 g/min., thereby giving moist spherical particles.

The moist spherical particles were charged in FL apparatus, and then dried under fluidized conditions at 60° C. After the drying was completed, vitamin C (sodium L-ascorbate) was coated on the dried spherical particles under the same fluidized conditions by spraying a 20wt % aqueous vitamin C (sodium L-ascorbate) solution (800 g) at a rate of 40 mL/min and then drying the resultant particles.

As a result, spherical particles were yielded which consisted essentially of vitamin C (sodium L-ascorbate) having particle sizes of 710–1000 μm (yield: 82%). The spherical particles had an aspect ratio of 1.09, a bulk density of 0.80 g/mL and an angle of repose of 31 degree. The individual spherical particles had a smooth surface just as that shown in FIG. 7, and had a friability of 0.39%.

Example 6

Sodium chloride crystals (1000 g), which has previously been sieved to 300–500 μm, were charged as cores on the rotary disc in CF apparatus and the rotary disc was rotated at 200 rpm while supplying slit air into the granulating vessel. Subsequently, spray granulation was performed by spraying water on the cores at a rate of 10 mL/min. under pressure at 0.8 kg/cm$^2$ while dispersing sodium chloride powder (1200 g) with an average particle size of 25.7 μm over the cores at a feed rate of 60 g/min., thereby giving moist spherical particles.

Figure 8:
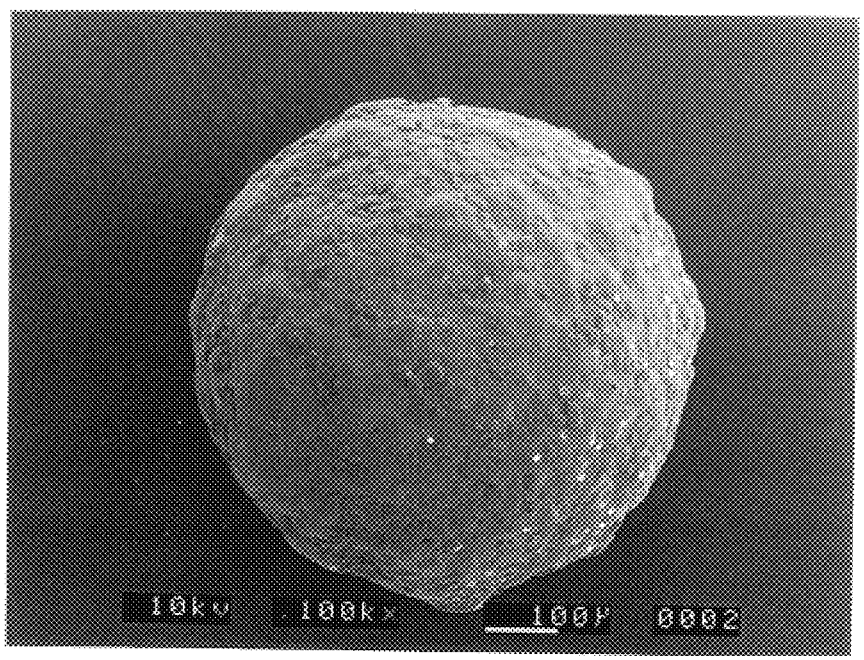
FIG. 8 is a photograph showing the surface condition of a spherical single-substance (sodium chloride) particle according to the present invention, as observed under an electron microscope.

The moist spherical particles were charged in FL apparatus, and then dried under fluidized conditions at 60° C., thereby yielding spherical particles consisting essentially of sodium chloride having particle sizes of 355–600 μm (yield: 75%). The spherical particles had an aspect ratio of 1.10, a bulk density of 1.09 g/mL and an angle of repose of 31 degree. The individual spherical particles had a smooth surface as shown in FIG. 8, and had a friability of 0.46%.

Example 7

D-Xylitol crystals (300 g) having particle sizes of 355–500 μm were charged on the rotary disc in a centrifugal tumbling granulating apparatus ("CF-360" model) and the rotary disc was rotated at 160–200 rpm while supplying slit air into the granulating vessel. Subsequently, spray granulation was performed by spraying a 50% aqueous D-xylitol solution onto the D-xylitol crystals at a rate of 5 mL/min. under pressure at 1.0 kg/cm$^2$ while dispersing crushed D-xylitol powder (2400 g) with an average particle size of 25.7 μm over the D-xylitol crystals, thereby giving moist spherical particles.

The moist spherical particles were charged in a fluidized bed granulating apparatus ("FLO-5" model), and then dried at 60° C. The resultant spherical particles (200 g) were charged in another fluidized bed granulating apparatus ("FLO-MINI" model) and spray coated with a 5wt % aqueous/ethanol solution of shellac (80 g) at a rate of 4 mL/min, thereby yielding spherical particles having particle sizes of 710–1000 μm (yield: 82.0%). The spherical particles had a longer diameter/shorter diameter ratio of 1.09, a bulk density of 0.710 g/mL and an angle of repose of 31 degree. The individual spherical particles had good surface smoothness as observed under a scanning electron microscope.

Comparative Example 1

The same procedures as in Example 7 were performed, except that a 5wt % aqueous HPC-L solution was used in place of the aqueous D-xylitol solution of Example 7. The obtained particles had a longer diameter/shorter diameter ratio of not smaller than 1.2, and therefore desired spherical particles could not be obtained.

Comparative Example 2

The moist spherical particles obtained in Example 7 were charged in a fluidized bed granulating apparatus ("FLO-5" model) and dried at 60° C. In this manner, spherical particles having particle sizes of 710–1000 μm were obtained (yield: 83.2%). The spherical particles had a longer diameter/shorter diameter of 1.09, a bulk density of 0.706 g/mL and an angle of repose of 31 degree. However, the surface of the individual particles was never smooth, on which powdery materials of the order of several tens μm were adhered. Moreover, when the spherical particles were left to stand at room temperature for several hours, they caused to agglomerate due of the hygroscopic properties of D-xylitol.

Example 8

The spherical particles (200 g) obtained in Comparative Example 2 were charged in a fluidized bed granulating apparatus ("FLO-MINI" model) and spray coated with a 6wt % aqueous ethanol solution of zein (66.7 g) at a rate of 5 mL/min, thereby yielding spherical particles having particle sizes of 710–1000 μm (yield: 82.2%). The spherical particles had a longer diameter/shorter diameter ratio of 1.09, a bulk density of 0.715 g/mL and an angle of repose of 31 degree. The individual spherical particles had a smooth surface without adhesion of any crystalline matters as observed under a scanning electron microscope. When the spherical particles were left to stand at room temperature, no agglomeration was observed.

Example 9

The spherical particles (200 g) obtained in Comparative Example 2 were charged in a fluidized bed granulating apparatus ("FLO-MINI" model) and spray coated with a 5wt % ethyl acetate solution of polyvinyl acetate (80 g) at a rate of 4 mL/min, thereby yielding spherical particles having particle sizes of 710–1000 μm (yield: 81.4%). The spherical particles had a longer diameter/shorter diameter ratio of 1.09, a bulk density of 0.714 g/mL and an angle of repose of 31 degree. The individual spherical particles had a smooth surface without adhesion of any crystalline matters as observed under a scanning electron microscope. When the spherical particles were left to stand at room temperature, no agglomeration was observed.

Comparative Example 3

The spherical particles (200 g) obtained in Comparative Example 2 were charged in a fluidized bed granulating apparatus ("FLO-MINI" model) and spray coated with a 5wt % aqueous HPMC solution (80 g) at a rate of 4 mL/min, thereby yielding spherical particles having particle sizes of 710–1000 μm (yield: 80.3%). The spherical particles had a longer diameter/shorter diameter ratio of 1.09, a bulk density of 0.716 g/mL and an angle of repose of 31 degree. The individual spherical particles had a smooth surface without adhesion of any crystalline matters as observed under a scanning electron microscope. However, when the spherical particles were left to stand at room temperature, they caused to agglomerate.

Example 10

The spherical D-mannitol particles (3 kg) obtained in Example 1 were charged in a centrifugal fluidized bed granulating apparatus (CF-360" model manufactured by Freund Industrial Co., Ltd.), and the rotary disc was rotated at 200 rpm while supplying slit air. Subsequently, coating granulation was performed by spraying a 2% solution of ethyl cellulose in ethanol on the spherical particles at a rate of 4–6 g/min. while gradually dispersing phenylpropanolamine hydrochloride powder (2.7 kg) over the spherical particles, thereby giving crude granules. The crude granules (5 kg) were charged in a fluidized bed granulating apparatus ("WSG-5" model; Okawara Mfg. Co., Ltd.) and caused to fluidize by supplying dry air of 50° C. A 15wt % aqueous mannitol solution (coating solution), which comprised triethyl citrate as a plasticizer and talc as a lubricant in an aqueous ethyl cellulose dispersion ("Aquacoat®"; Asahi Chemical Industry Co., Ltd.), was sprayed on the spherical particles in the apparatus at a rate of 15 g/min. The resultant particles were then cured at 60° C. for 5 hours, thereby yielding sustained-release granules.

Comparative Example 4

Figure 1:
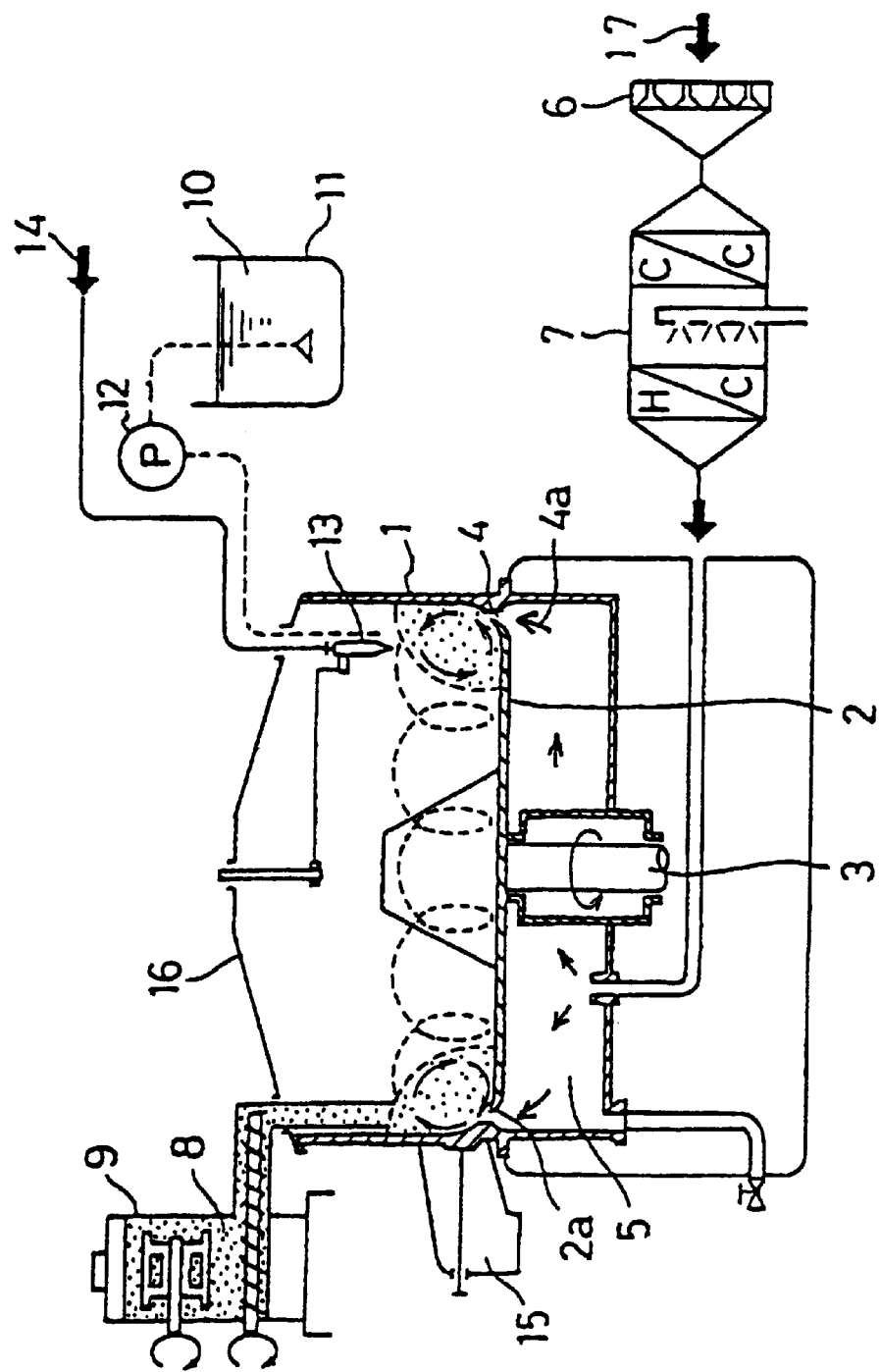
FIG. 1 is a schematic illustration of an example of the coating granulation apparatus applicable in the present invention, wherein the individual numerals refer to the following components: 1 granulating vessel; 2 rotary disc; 3 rotating shaft; 4 slit; 5 air chamber; 6 dehumidifier; 7 heat exchanger; 8 powdery single-substance particle; 9 dispersing device; 10 spraying liquid; 11 tank; 12 constant flow pump; 13 spray nozzle; 14 spraying air; 15 product ejection device; 16 stator cover; 17 air served as the slit air.
Figure 2:
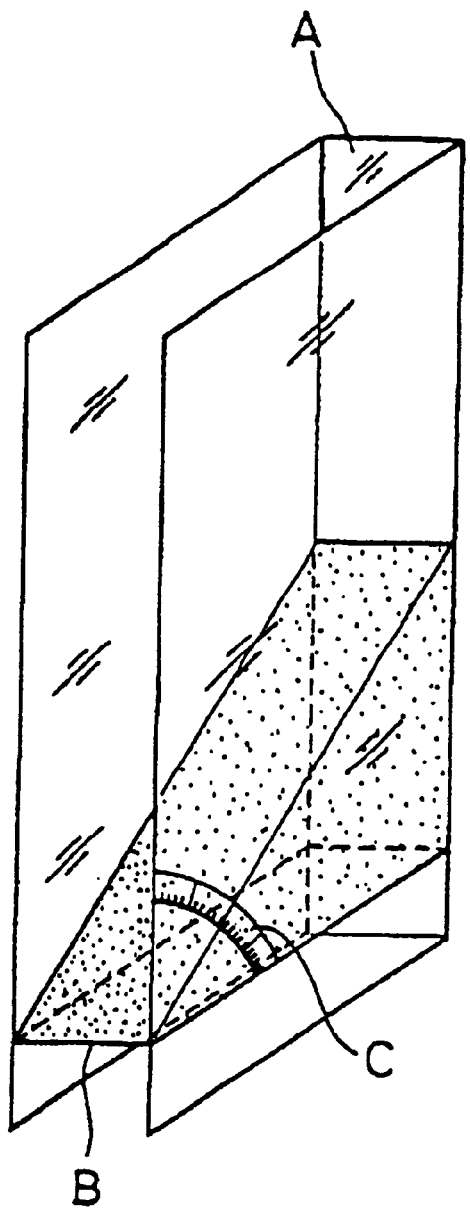
FIG. 2 is an explanatory illustration of the method for determining the angle of repose of spherical single-substance particles.
Figure 3:
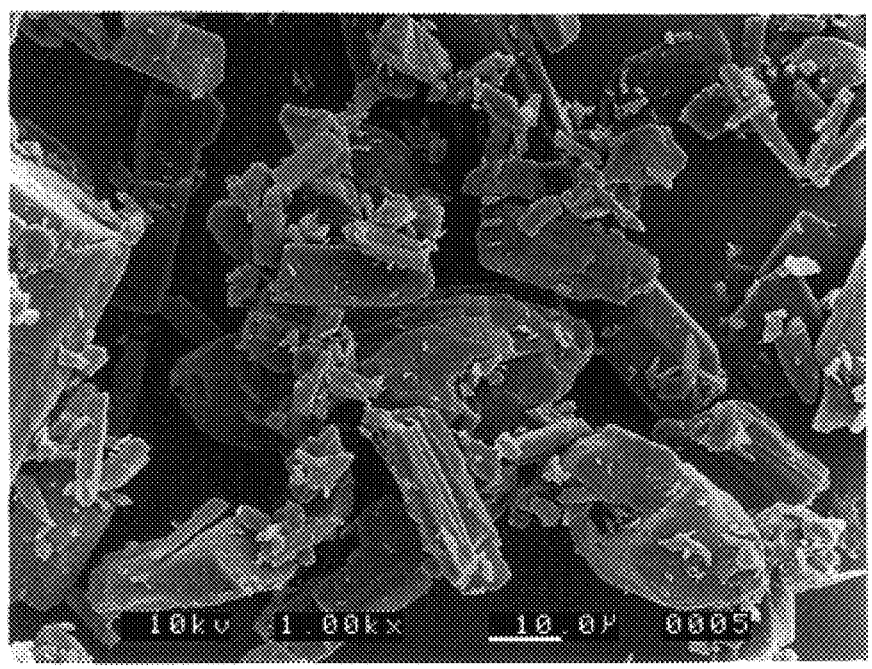
FIG. 3 is a photograph showing the surface condition of a powdery single substance (powdery D-mannitol) applicable in the present invention, as observed under a scanning electron microscope (i.e., SEM).
Figure 4:
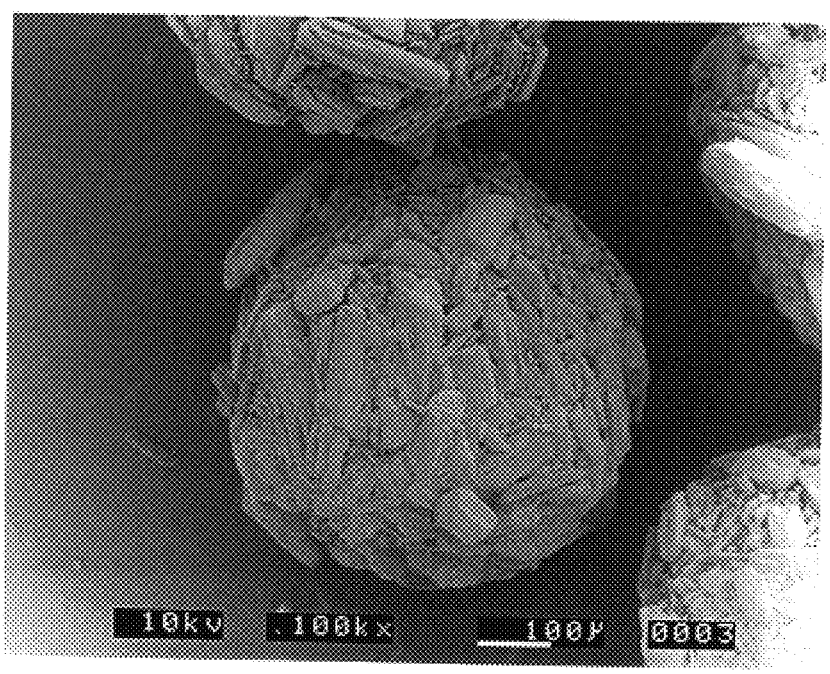
FIG. 4 is a photograph showing the surface condition of a spherical single-substance (D-mannitol) particle without fixation treatment, as observed under an electron microscope.

The moist spherical particles obtained in Example 1 were charged in FL apparatus and dried at 60° C., thereby yielding spherical D-mannitol particles having particle sizes of 500–710 μm (yield: 81.8%). The spherical particles had an aspect ratio of 1.09, a bulk density of 0.69 g/mL and an angle of repose of 31 degree. As shown in FIG. 4, the spherical particles had powdery matters of the orders of several tens μm adhered thereon. Moreover, due to their poor surface smoothness, the spherical particles exerted an abrasiveness as large as 11.3%.

Comparative Example 5

The D-Mannitol granule cores (212–355 μm) (1 kg) obtained in Example 2 were charged in CF-360 apparatus, and the rotary disc was rotated at 180 rpm while supplying slit air therein. Subsequently, spray granulation was performed for 40 min. by spraying a 5 wt % aqueous solution (240 mL) of hydroxypropyl cellulose ("HPC-L" made by Nippon Soda Co., Ltd.) under pressure at 0.8 kg/cm$^2$ while dispersing D-mannitol powder having an average particle size of 7.4 μm (1 kg) at a feed rate of 25 g/min for 40 min.

In this process, there was a large amount of powder remaining in the apparatus without adhering onto the spherical particles, and many of the resultant spherical particles were coarse and larger. The spherical particles had an aspect ratio of not smaller than 1.2, and therefore desired spherical particles could not be obtained.

Comparative Example 6

The moist spherical particles obtained in Example 4 were charged in FL apparatus and dried at 60° C., thereby yielding spherical particles having particle sizes of 355–600 μm (yield: 73%). The spherical particles had an aspect ratio of 1.10 and, as an aggregate, had a bulk density of 0.81 g/mL and an angle of repose of 31 degree.

Figure 6:
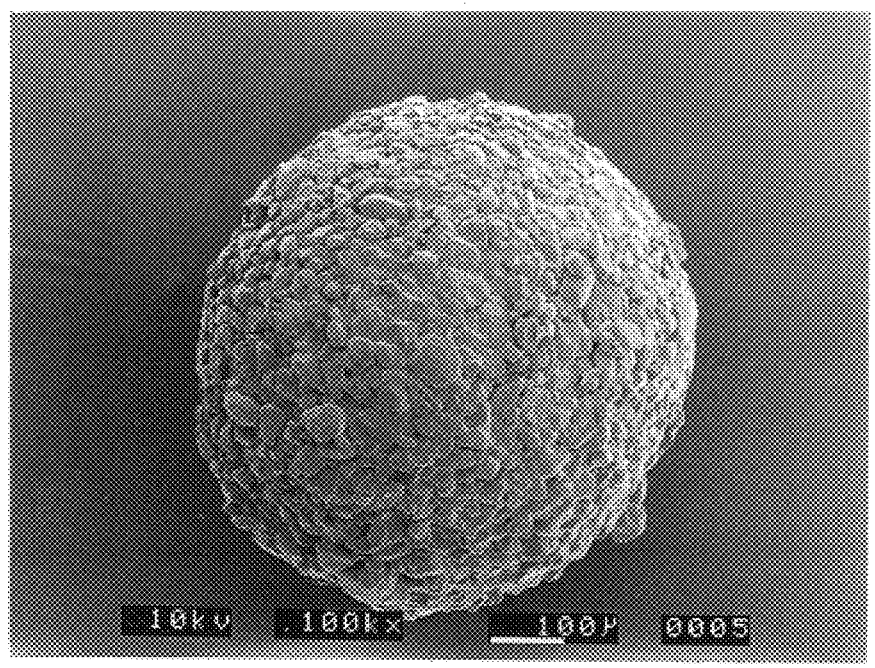
FIG. 6 is a photograph showing the surface condition of a spherical single-substance (L-ascorbic acid) particle without fixation treatment, as observed under an electron microscope.

As shown in FIG. 6, the spherical particles had adhesion of powdery vitamin C (L-ascorbic acid) of the orders of several tens μm thereon. Moreover, due to their poor surface smoothness, the spherical particles exerted an abrasiveness as large as 10.40%.

Comparative Example 7

The same procedures as in Example 6 were performed, except that a 5wt % aqueous HPC-L solution was used in place of water of Example 6. The resultant granulated particles had an aspect ratio exceed 1.2, and therefore desired spherical particles could not be obtained.

When compared Example 6 with Comparative Example 7, it is found that the use of a water-soluble polymer (e.g., HPC-L) as a binder makes it impossible to form spherical particles, due the high binding strength of the water-soluble polymer.

The comparison between Example 6 and Comparatove Example 7 also reveals that when a water-soluble polymer such as HPC-L is used in place of water, the water-soluble polymer is necessary to be used in the form of a diluted aqueous solution so that the binding strength of the water-soluble polymer as a binder becomes weakened. The concentration of such a diluted aqueous solution of a water-soluble polymer can be decided experimentally for each water-soluble polymer.

Test Example 1

To further study the applicability of different additives as the raw materials of the spherical particles of the present invention, the compatibility with phenylpropanolamine hydrochloride was examined by thermal analysis. The results are shown in Table 2.

TABLE 2

| Additives | T (° C.) |
|---|---|
| Medicinal agent alone (kneaded amount: 10 mg) | 229.9 |
| Examples | |
| D-Mannitol | 228.2 |
| Xylitol | 215.3 |
| Reference Examples | |
| Lactose | 171.3 |
| Crystalline cellulose | 218.3 |
| Corn starch | 186.1 |
| Pure sucrose | 143.8 |

Measurement conditions:
(1) the medicinal agent and each additive were kneaded in an amount of 5 mg each (kneading);
(2) Measuring temperatures: 25° C.→250° C.;
(3) Temperature-rising rate: 5° C./min.; and
(4) T: a temperature at which rapid thermal decomposition begins to occur.

These results demonstrate that, as the raw material having a smaller interaction with phenylpropanolamine hydrochloride, the additives of the present invention (in Table 2, indicated as "Examples") are preferable compared to the conventionally used additives (in Table 2, indicated as "Reference Examples"), and that the combination of D-mannitol with phenylpropanolamine hydrochloride causes less decrease in the thermal decomposition starting temperature compared to that with phenylpropanolamine hydrochloride alone.

Test Example 2

The granule product containing phenylpropanolamine hyrdochloride as a pharmaceutically active component according to the present invention was examined for the storage stability. In this test example, a granule product comprising spherical D-mannitol particles prepared in Example 7 was used as the base of a test product and a granule product comprising spherical crystalline cellulose particles was used as a base of a control. The results are shown in Table 3.

TABLE 3

| Component of spherical particles | Storage conditions | ΔE | Appearance |
|---|---|---|---|
| Crystalline cellulose | 60° C., for 3 days | 7.30 | Dark yellow |
|  | for 14 days | 12.45 | Brown |
| D-mannitol | 60° C., for 3 days | 1.98 | White |
|  | for 14 days | 3.00 | Pale yellowish white |

(ΔE: Color changed)

As a result, it was found that the granule product mainly comprising D-mannitol showed remarkably higher storage stability than that mainly comprising crystalline cellulose.

INDUSTRIAL APPLICABILITY

As described above, the spherical single-substance particles of the present invention have an advantage that they are low-calorie or non-calorie compared to conventional sucrose-based (or sucrose/starch-based) spherical particles, because it consists mainly of crystals of a sugar alcohol, vitamin C, sodium chloride or the like. Moreover, unlike spherical particles comprising mainly highly water-soluble crystalline cellulose, the spherical particles of the present invention exert adequate disintegrating properties. Accordingly, the spherical particles of the present invention had ideal properties as the cores for controlled-release pharmaceutical preparations.

In addition, the fixation treatment of the spherical particles provides surface smoothness of the spherical particles, leading to uniformity in the coating thickness of a medicinal agent layer or a release-controlling layer coated on the spherical particles. As a result, it becomes possible to control the thickness of a release-controlling layer which may influence on the release rates of the medicinal agent or to control the amount of the medicinal agent so as to be maintained at an effective blood level. Thus, sustained-release preparations can be designed optimally for intended application.

Since the spherical single-substance particles of the present invention are surface-treated by fixation treatment, they have good surface smoothness and low abrasiveness. Therefore, when used in the preparation of a sustained-release preparation or the like, the spherical particles advantageously provide increased granulation and coating efficiencies, leading to improved production efficiency and reduced cost.

The spherical particle itself can contain a medicinal agent. Therefore, for example, by applying a layer containing additional medicinal agent and a release-controlling layer on the medicinal agent-containing spherical particle, a sustained-release preparation having three layers can be produced. Alternatively, a plurality of release-controlling layers may also be applied which have different composition so that several levels of pH-dependent solubility are provided. Thus, the production of unprecedented type of sustained-release preparations becomes possible.

Since the spherical particle of a sugar alcohol or sodium chloride as a single substance of the present invention consists of only the single substance or contains the single substance in a very large proportion, it is less reactive with a medicinal agent, and therefore can advantageously be mixed with a medicinal agent. In particular, in the past, it has been impossible to produce smooth-surfaced spherical particles consisting of only a single substance. The present invention enables to provide such spherical particles in the pharmaceutical industry for the first time.

The spherical particles of a sugar alcohol or sodium chloride as a single substance of the present invention, which consist only of the single substance or contain the single substance in a very large proportion, cause no Maillard reaction or, if any, less Maillard reaction, and therefore can advantageously be mixed with a food or a food additive. In particular, in the past, it has been impossible to produce smooth-surfaced spherical particles consisting of only a single substance. The present invention enables to provide such spherical particles in the food industry for the first time.

The spherical vitamin C particles of the present invention consist only of vitamin or containing vitamin C in a very large proportion. In the past, it has been impossible to produce such spherical particles with smooth surfaces. The present invention enables to provide such spherical particles in the pharmaceutical and food industries for the first time.

What is claimed is:

1. A spherical particle comprising a granulated particle containing at least 95 wt % of a water-soluble single substance selected from the group of such substances consisting of a sugar alcohol, vitamin C and sodium chloride which has a viscosity of 10 mPa.s or less as determined in the form of a saturated aqueous solution at 25–45° C., the spherical particle having an aspect ratio of 1.2 or less and, as an aggregate, having a bulk density of 0.65 g/mL or more and an angle of repose of 35 degree or less.

2. The spherical particle of claim 1, wherein the sugar alcohol is D-mannitol and/or erythritol.

3. The spherical particle of claim 1, wherein the vitamin C is L-ascorbic acid and/or sodium L-ascorbate.

4. The spherical particle of claim 1, wherein the single substance comprises at least 95 wt % of xylitol.

5. A process for producing the spherical particles of claim 1, the process comprising the steps of:

preparing moist spherical particles of a water-soluble single substance selected from the group of such substances consisting of a sugar alcohol, vitamin C and sodium chloride having a viscosity of 10 mPa.s or less as determined in the form of a saturated aqueous solution at 25–45° C., by charging, as cores, granulated particles of the single substance on a rotary disc in a processing vessel of a centrifugal tumbling apparatus, wherein the granulated particles are prepared by granulating a powder of the single substance over the cores and simultaneously spraying on the cores at least one liquid selected from the group consisting of water, an aqueous solution of the single substance and a diluted aqueous solution of a water-soluble polymer, while both rotating the rotary disc and supplying slit air into the vessel; and fixation-treating the moist spherical particles by drying them while spraying an aqueous solution of the single substance and/or a diluted aqueous solution of the single substance and/or a diluted aqueous solution of the water-soluble polymer in a fluidized bed apparatus.

6. A process for producing the spherical particles of claim 1, the process comprising the steps of:

preparing moist spherical particles of a water-soluble single substance selected from the group of such substances consisting of a sugar alcohol, vitamin C and sodium chloride having a viscosity of 10 mPa.s or less as determined in the form of a saturated aqueous solution at 25–45° C., by charging, as cores, crystalline particles of the single substance on a rotary disc in a processing vessel of a centrifugal tumbling apparatus; and then dispersing powdery particles of the single substance over the cores and simultaneously spraying on the cores at least one liquid selected from the group consisting of water, an aqueous solution of the single substance and a diluted aqueous solution of a water-soluble polymer, while both rotating the rotary disc and supplying slit air into the vessel; and fixation-treating the moist spherical particles by drying them while spraying an aqueous solution of the single substance and/or a diluted aqueous solution of the water-soluble polymer in a fluidized bed apparatus.

7. A process for producing spherical particles each consisting essentially of an aggregate of sodium chloride crystal microparticles containing at least 95 wt % of sodium chloride having a viscosity of 10 mPa.s or less as determined in the form of a saturated aqueous solution at 25–45° C., the process comprising the steps of:

preparing moist spherical particles of sodium chloride by charging, as cores, sodium chloride crystal particles on a rotary disc in a processing vessel of a centrifugal tumbling apparatus; and then dispersing sodium chloride crystal microparticles which were previously been crushed over the cores and simultaneously spraying on the cores at least one liquid selected from the group consisting of water, an aqueous sodium chloride solution and a diluted aqueous solution of a water-soluble polymer, while both rotating the rotary disc and supplying slit air into the vessel; and drying the moist spherical particles in a fluidized bed apparatus.

8. A process for producing spherical particles consisting essentially of xylitol crystal particles having a viscosity of 10 mPa.s or less as determined in the form of a saturated aqueous solution at 25–45° C., the process comprising the steps of:

preparing moist particles of xylitol by charging, as cores, xylitol crystal particles on a rotary disc in a processing vessel of a centrifugal tumbling apparatus; and then dispersing powdery xylitol particles over the cores and simultaneously spraying on cores at least one liquid selected from the group consisting of water, an aqueous xylitol solution and a diluted aqueous solution of a water-soluble polymer, while both rotating the rotary disc and supplying slit air into the vessel; and fixation-treating the moist spherical particles by drying them while spraying shellac-containing aqueous ethanol solution or vinyl acetate resin-containing ethyl acetate in a fluidized bed apparatus.

9. The process of claim 5, wherein the single substance is D-mannitol and/or erythritol.

10. The process of claim 5, wherein the single substance is L-ascorbic acid and/or sodium L-ascorbate.

11. A spherical particle for use in the production of a food preparation, comprising the spherical particle of any one of claim 1.

12. A spherical particle for coating granulation in the production of a food, comprising the spherical particle of any one of claim 1.

13. A spherical particle for coating granulation in the production of a pharmaceutical preparation, comprising the spherical particle of claim 1.

14. The spherical particle for coating granulation in the production of a pharmaceutical preparation of claim 13, wherein the spherical particle is a substance comprising a sugar alcohol.

15. A pharmaceutical preparation comprising the spherical particle of claim 13.

16. The pharmaceutical preparation of claim 15, which contains phenylpropanolamine hydrochloride as a pharmaceutically active component.

17. The pharmaceutical preparation of claim 15, wherein the pharmaceutical preparation is in the form of granules or capsules.

18. A process for producing a pharmaceutical preparation, comprising using the spherical particles for coating granulation of claim 13 as a carrier.

19. The process of claim 6, wherein the single substance is D-mannitol and/or erythritol.

20. The process of claim 6, wherein the single substance is L-ascorbic acid and/or sodium L-ascorbate.

* * * * *